United States Patent
Weissmahr

(12)
(10) Patent No.: US 6,511,685 B1
(45) Date of Patent: Jan. 28, 2003

(54) DIETARY SUPPLEMENT DERIVED FROM FERMENTED MILKS FOR THE PREVENTION OF OSTEOPOROSIS

(75) Inventor: Joseph A. Weissmahr, Zürich (CH)

(73) Assignee: Sigma-Tau Healthscience S.p.A., Pomezia (IT)

( * ) Notice: Subject to any disclaimer, the term of this patent is extended or adjusted under 35 U.S.C. 154(b) by 0 days.

(21) Appl. No.: 09/719,170

(22) PCT Filed: Apr. 7, 2000

(86) PCT No.: PCT/IT00/00130

§ 371 (c)(1),
(2), (4) Date: Dec. 13, 2000

(87) PCT Pub. No.: WO00/60950

PCT Pub. Date: Oct. 19, 2000

(30) Foreign Application Priority Data

Apr. 13, 1999 (CH) ................................................ 0683/99

(51) Int. Cl.⁷ ................................................ A23L 1/304
(52) U.S. Cl. .............................. 426/2; 426/34; 426/42; 426/43; 426/60; 426/62
(58) Field of Search ................................ 426/2, 34, 42, 426/43, 60, 62

(56) References Cited

U.S. PATENT DOCUMENTS 4,902,517 A * 2/1990 Nakagawa et al. ........... 426/42
5,820,903 A * 10/1998 Fleury et al. .................. 426/74
2001/0014322 A1 * 8/2001 Chen et al. ............... 424/93.45

* cited by examiner

*Primary Examiner*—Helen Pratt
(74) *Attorney, Agent, or Firm*—Oblon, Spivak, McClelland, Maier & Neustadt, P.C.

(57) ABSTRACT

A process is described for manufacturing dietary supplements (food integrators) by means of a natural fermentation, including the following steps: a) preparation of a "mix" at a 18° Centigrade temperature, containing one or more types of pasteurized milk from animal origin; b) introduction in such a "basic material" of a 1.5–4.5% in weight of polysaccharide "grains" mainly formed "friendly bacteria"; c) maintenance of the previous substance at a 18–25° Centigrade temperature for a first period of 6–12 hours then adding a quantity of 1–3 % in weight of a second pool of polysaccharide "grains", mainly formed by yeasts; d) maintenance of the substance at 18–25 ° C. during a second period of 6–12 hours, by adding again 2.5–65% in weight of "grains" mainly formed by yeasts, then adding some minerals (calcium, magnesium, etc.) in proportion 0.2–1.2% of weight; e) separation, by filtration, of different components of the substance, among whose a "residual matrix" composed by grains of polysaccharides containing bacteria and yeasts; f) drying of the substance, after filtration, for obtaining a fine powder, g) preparation of various dietary supplements, presented in tablets or "sachets" or other formulations, useful in the treatment of osteoporosis and other degenerative conditions.

22 Claims, No Drawings

DIETARY SUPPLEMENT DERIVED FROM FERMENTED MILKS FOR THE PREVENTION OF OSTEOPOROSIS

The present invention relates to products used as dietary supplements or nutritional supplements for the supplementation of nutrition and diets by taking substances, mainly of natural origin, which supply elements necessary for nutrition and thus for good maintenance of essential body functions (such as the formation and preservation of the bones, muscles, skin, its related tissues and the like).

More particularly, the present invention relates to a process for obtaining a natural dietary supplement which has proved very effective in the prevention and treatment of osteoporosis and of other diseases mainly due to calcium, magnesium and potassium deficiencies in the body.

At the present state of our technical and scientific knowledge, it is well known that an adequate supply of a number of nutritional substances, commonly called "nutrients" (such as minerals, vitamins, proteins, and others) is of fundamental importance for the proper development of body tissues and for the body's vital functions and that deficiencies or imbalances of such nutrients are often concomitant with actual pathological conditions (particularly those of a "degenerative" and/or chronic type which may affect various parts of the body, e.g. the skeleton and blood vessels, interalia.

It is also known that the main nutrients are ingested with the diet and, therefore, that, if the latter is sufficiently appropriate and balanced and if the body is in a normally functioning state in terms of the assimilation and conversion of such nutrients, there should be no problems with regard to the maintenance of conditions of good health from this point of view. In actual fact, it often happens that an individual's diet, even or, indeed, above all in the industrialised countries, presents imbalances due to deficiencies and/or excesses which in the course of time may cause serious damage to health. Many diseases, which are then treated with various drugs, are also often due to an unbalanced nutritional intake and it is well known that these could be prevented or even cured by restoring the lost equilibrium.

It is also known, moreover, that numerous products commonly coming under the definition of dietary supplements have been produced and used to solve the above-mentioned problems and are, therefore, a familiar aspect of the present state of the art. These supplements consist of combinations of various substances (nutrients) obtained by processes of chemical synthesis or extraction of various materials (vitamins, minerals of plant or animal origin) compounded in a particular formula and presented in the form of tablets or capsules or other types of preparations which can be orally taken. The administration of these preparations presents a whole series of drawbacks, the most important of which are: 1) the origin of the nutrients used (obtained by synthesis or extraction), which is often unsuitable for the human body; 2) difficulties of assimilation due to the source and type of the materials used, which substantially limit the bioavailability of the substances administered; 3) the respective proportions of the various nutrients present in the product administered, often predetermined independently of one another, without due regard for the equilibria actually to be found in nature and in metabolic processes and which constitute one of the key factors for the above-mentioned balanced diet required for effective conditions of health and well-being of the body.

As a consequence of the considerations outlined here, the inventor of the present invention concluded that solutions to the aforesaid problems effectively useful for the health and equilibrium of the body should be sought in completely natural preparation processes, by "piloting" exclusively the chemical transformations brought about biologically by micro-organisms such as, for instance, lactobacteria and yeasts so as to influence them in the manner required.

The condition of good development and maintenance of the health of the musculo-skeletal system and in particular of the bones is acknowledged to be a fundamental, widespread health problem.

It is related both to problems of diet and to the use of certain drugs, as well as to the manifestation of degenerative processes as a result of ageing which may lead to the onset of osteoporosis (which consists in a reduced density and resilience of the bones with a consequent increase in their fragility) and of collateral conditions of an inflammatory and painful type leading even to the ultimate risk of sudden fractures (in this case not due to any obvious serious trauma). The subjects most "at risk" are women, particularly during or after the period of the menopause, and those individuals with a particular "genetic risk" who specific analyses have identified as being present in 15% or more of the overall population.

A number of drugs effective against this disease are currently available, but it has now been established that the best approach to both the prevention and therapy of osteoporosis must necessarily entail adequate dietary supplementation on the basis of minerals such as calcium and magnesium with the possible addition of vitamin $D_3$. Such "supplementation", however, is mostly implemented by administering poorly assimilated products of unsatisfactory biological quality containing inorganic calcium or calcium which, in any event, is not absorbed in the bowel owing to a series of factors which block its absorption to a substantial extent. As an alternative to such supplementation, diets rich in milk and cheese products are often recommended; these provide a good supply of calcium (and also magnesium), but unfortunately present many problems which are often underestimated, such as: a) problems of poor digestibility or even of lactose intolerance; b) excessively high cholesterol levels; c) unwanted intake of calories and fats.

The inventor of the present invention therefore sought a solution which would yield a product better able to overcome the above-mentioned problems, in the form of a supplement which was demonstrably efficacious, reliable and inexpensive, that is to say by developing a product which: 1) guarantees the supply of adequate amounts of calcium, magnesium and other nutrients which are useful for the bones and metabolism for the purposes of the musculoskeletal functions; 2) ensures assimilation of the various nutrients; 3) assures digestibility and avoids intolerance; and 4) possesses the characteristics of a wholly biocompatible biological substance.

For this purpose, the inventor has found a process which is the subject matter of the present invention, which is delineated in the preamble of claim 1 and whose inventive features are disclosed in the characterizing part of said claim.

The present invention also relates to the dietary supplements obtainable with said process and their use for the prevention and therapy of osteoporosis and of other diseases due substantially to calcium, magnesium and potassium deficiencies.

The process according to the invention makes it possible to obtain a "nutrient complex", by which definition is meant a nutritional substance of natural origin, which is the result of biological processing by micro-organisms (the so-called "beneficial micro-organisms", such as lactobacilli, etc.), containing all the nutrients desired, and particularly calcium, magnesium and potassium, with the desired characteristics of good assimilation, tolerability and efficacy. The inventor started out by selecting the products obtainable from various types of fermented milk, products which differ both in the type of milk (cow, sheep, goat, mare) and the type of micro-organisms used, as well as in the modalities whereby the fermentation process itself is conducted. A particular type of fermentation product was thus identified, which is akin to a substance traditionally known in countries of the Middle East and Eastern Europe under the name Kefir, endowed with optimal characteristics as a "nutrient complex".

Kefir is a kind of yoghurt, obtainable by fermentation of milk through the dual action of a number of lactobacilli and yeasts, the appropriate combination of which makes it possible to obtain a biologically processed product with the required characteristics. The addition, during the fermentation process, of desired substances (for example, though not exclusively, calcium) allows "enrichment" of the nutrient complex so that it can be used specifically for a certain type of application (for example, for the treatment of osteoporosis). It is the micro-organisms that process one or more minerals, fixing them in their cells and ensuring their bioavailability.

To achieve the desired objectives, the inventor, after meticulously studying the traditional natural processes implemented in the areas mentioned above, concluded that natural food supplements with a highly effective action could be obtained through the processing work of a suitable mixture of micro-organisms in a predetermined sequence, by modifying said processes with targeted additions of useful substances and by appropriately modifying the times and temperatures of the various steps of said processes.

Operating in this way, a process was found which is suitable for producing dietary supplements presenting a high degree of efficacy which reaches an adequate level for the supplements to be used for actual therapeutic purposes.

As is pointed out in the following part of this description, a dietary supplement obtained by means of the process according to the present invention, as a result of the broad spectrum and high concentrations of organic substances with beneficial effects that it contains, not only proves useful as a primary measure, as indicated earlier, for the prevention and therapy of conditions due to calcium, magnesium and potassium deficiencies, but also exerts a secondary beneficial action on various other disorders generated by genetic factors in conjunction with functional imbalances of a chemical nature.

We shall now describe an embodiment, which is neither binding nor exclusive, of the process according to the present invention.

This process comprises essentially the following steps:
a) preparing a mixture at 18° C. comprising one or more types of pasteurised milks of animal origin;
b) adding to said mixture 1.5–4.5% by weight of first granules consisting prevailingly of bacteria;
c) holding the mixture at 18–25° C. for an initial time period ranging from 6 to 12 hours and subsequently adding, after approximately half the process, 1–3% by weight of said pasteurised milk mixture;
d) adding to the mixture 2.5–6.5% by weight of second granules consisting prevailingly of yeasts;
e) holding the mixture thus obtained at 18–25° C. for a second time period ranging from 6 to 12 hours and adding thereto calcium and/or magnesium and/or potassium in amounts of 0.2–1.2% by weight during the first half of said second time period;
f) filtering off a residual matrix consisting of the granules introduced in the various steps of the process and the granules formed during the process itself;
g) drying the mixture after said filtration so as to obtain a powder.

Said first and second granules can be obtained by means of a conventional-type milk inoculation process, starting from commercially available Kefir granules. For the control and identification of the bacteria for the standardization of the contents of said granules reference can be made to the texts by M. Montage et al. (1997), Kandler-Weiss (1986) and Hardle (1986) for said first granules consisting mainly of bacteria, and to the method of Barnet (1990) for the second granules consisting mainly of yeasts. All the aforesaid publications are incorporated herein by reference. An indicative profile of the contents of said granules can be deduced from the attached Tables A and B, which describe the types and numbers (per gram) of bacteria or yeasts in the granules.

| First granules (Table A) | Mainly bacteria | |
|---|---|---|
| Lactobacillus brevis | $10^6$–$10^7$ | |
| Lactobacillus casei | $10^6$–$10^7$ | |
| Lactobacillus plantarum | $10^6$–$10^7$ | |
| Lactobacillus kefir | $10^8$–$10^9$ | (optionally, "addition" of 20–30%) |
| Lactobacillus kefiranofaciens | $10^7$–$10^8$ | (optionally, "addition" of 20–30%) |
| Acetobacter aceti | $10^6$–$10^7$ | |
| Leuconostoc mesenteroides | $10^5$–$10^6$ | |
| Streptococcus lactis | $10^4$–$10^5$ | |
| Others | $10^5$–$10^6$ | |
| Saccharomyces lactis | $10^3$–$10^4$ | |
| Saccharomyces cerevisiae | $10^5$–$10^6$ | |
| Saccharomyces fragilis | $10^4$–$10^5$ | |
| Candida kefir | $10^4$–$10^5$ | |

| Second granules (Table B) | Mainly yeasts |
|---|---|
| Lactobacillus brevis | $10^5$–$10^6$ |
| Lactobacillus casei | $10^5$–$10^6$ |
| Lactobacillus plantarum | $10^5$–$10^6$ |
| Lactobacillus kefir | $10^6$–$10^7$ |
| Lactobacillus kefiranofaciens | $10^6$–$10^7$ |
| Acetobacter aceti | $10^5$–$10^6$ |
| Leuconostoc mesenteroides | $10^4$–$10^5$ |
| Streptococcus lactis | $10^4$–$10^5$ |
| Others | $10^5$–$10^6$ |
| Saccharomyces lactis | $10^5$–$10^6$ |
| Saccharomyces cerevisiae | $10^6$–$10^7$ |
| Saccharomyces fragilis | $10^5$–$10^6$ |
| Candida kefir | $10^6$–$10^7$ |
| Others | $10^5$–$10^6$ |

The distinctive characteristics of a dietary supplement thus obtained, due to the particular mix of bacilli and yeasts, and which remarkably improve over the above-mentioned Kefir (and other yoghurts as well) are mainly the following:

1. Among biological substances high in minerals such as calcium, magnesium and potassium, said dietary supplement surprisingly presents a profile which is much richer in other "noble" substances, as an adjunct to the specific supplementation and of general value, such as branched-chain amino acids, polysaccharides and vitamins. These nutrients have been shown to significantly enhance the intestinal absorption of calcium and the metabolism of various minerals.

2. The effect of the micro-organisms on lactose brings about its conversion into lactic acid, which, in turn, is an "enhancer" of the absorption of calcium, in addition to reducing the risks of lactose intolerance. To this should be added the fact that the micro-organisms themselves produce an enzyme, galactosidase, which makes lactose digestible. Lastly, they are capable of substantially reducing the absorption of cholesterol, thereby protecting the body against a well-known threat.

3. The presence of polysaccharides (slow-uptake carbohydrates) also makes this product suitable for diabetics and for elderly patients in general. The branched-chain amino acids are also important elements for elderly subjects by virtue of their basic function in the growth and maintenance of muscle fibres (thereby again providing additional support for the entire musculoskeletal system).

Presented here below is a detailed indicative profile of the constituents of the product concerned. First, an example is given Tables 1 to 5) of a formulation (nutrient complex) selected using a fermentation process according to the invention, aimed at providing supplementation of minerals such as calcium, magnesium and potassium, according to the criteria of the invention itself, this is followed by the presentation (Table 6) of the composition of a dietary supplement, produced by means of "targeted enrichment" of the starting substance and suitable for preventive and therapeutic applications in the field of osteoporosis:

Composition of fermentation substances obtained by means of the process according to the invention.

TABLE 1

General analysis

| Constituents | % | ±% |
|---|---|---|
| Protein | 45 | 15 |
| Moisture | 5 | 10 |
| Fat | (1) | |
| Total lipids | 4 | 2 |
| Fiber | 3 | 2 |
| Carbohydrates | 30 | 10 |
| Minerals (ash) | 13 | 8 |
| Calories per gram | 2.8 | |

TABLE 2

Minerals (mg per 100 g product)

| Constituents | | (±%) |
|---|---|---|
| Potassium | 2240 | 20 |
| Phosphorus | 1320 | 15 |
| Magnesium | 180 | 30 |
| Sodium | 680 | 15 |
| Calcium | 1660 | 20 |
| Zinc | 2.3 | 20 |
| Iron | 4.5 | 10 |
| Chromium | 146 μg | |
| Selenium | 13.3 μg | |
| Copper | 0.3 | 20 |
| Manganese | Traces | |

TABLE 3

Vitamins (mg per 100 g product)

| Constituents | (±25%) |
|---|---|
| $B_1$ (thiamine) | 6.6 |
| $B_2$ (riboflavin) | 5.6 |

TABLE 3-continued

Vitamins (mg per 100 g product)

| Constituents | (±25%) |
|---|---|
| Niacin | 54 |
| $B_6$ (pyridoxine HCl) | 4 |
| $B_{12}$ | 50 μg |
| Folic acid | 1.4 |
| Biotin (H) | 180 μg |
| Inositol | 300 |
| Choline | 453.3 |
| Para-aminobenzoic acid | 2.4 |

TABLE 4

Amino acids (mg per 100 g product)

| Constituents | (±20%) |
|---|---|
| Arginine | 3200 |
| Glutamic add | 13100 |
| Hystidine | 2000 |
| Isoleucine | 4300 |
| Leucine | 7500 |
| Lysine | 6700 |
| Methionine | 1400 |
| Phenylalanine | 3500 |
| Threonine | 5200 |
| Tryptophan | 1800 |
| Tyrosine | 3200 |
| Valine | 4800 |
| | 56700 |

TABLE 5

Nucleic acids

| Constituents | (±30%) |
|---|---|
| Total | 8–9% |

Example of dietary supplement for osteoporosis.

TABLE 6

Content (to roughly 5% approximation)

| Value in g | 100 g | Sachet (10 g) | 2 tablets (12 g) |
|---|---|---|---|
| Protein | 45 | 4.5 | 5.40 |
| Carbohydrates | 30 | 3.0 | 3.60 |
| Fat | 1 | 0.1 | 0.12 |
| Total lipids | 4 | 0.4 | 0.48 |
| Fibre | 3 | 0.3 | 0.36 |
| Minerals | 13 | 1.3 | 1.56 |
| Moisture | 4 | 0.4 | 0.48 |
| Calories | 280 | 28.0 | 33.60 |

The dietary supplements produced via the process of the present invention have been extensively tried and tested, demonstrating that they effectively possess the characteristics desired, which allow remarkable advantages over traditional calcium supplements to be obtained. The main advantages which are particularly worth mentioning are as follows:

The presence in the supplements thus obtained of substantial amounts of calcium and other minerals in greater quantities than in the commonly used dietary supplements.

A high degree of intestinal absorption and bioavailability of the minerals contained in the supplement for the bones and the body and, therefore, a greater efficiency and efficacy compared to the commonly used products.

A high degree of tolerability of the supplement, much greater than that of milk-dairy products, as a result of solving the lactose problem.

Lower amounts of cholesterol absorbed compared to various milk-dairy products recommended in diets for osteoporosis.

Optimal efficacy due to the presence in the supplement of a complete nutritional profile of biological origin, and not a simple "mix" of substances unrelated to each other. Among the "additional support" substances operating in conjunction with the mineral profile, a number of them afford actual advantages to be achieved which are unattainable with the other commonly recommended dietary supplements and nutritional substances:

branched-chain amino acids (beneficial for the entire musculoskeletal system)

polysaccharides (advantageous for the elderly and the diabetics vitamins (which complete the nutritional profile).

The substance, obtainable by lyophilisation as a dry powder with an agreeable taste, is presented in very practical formulations, such as chewable tablets and sachets with the contents to be dissolved in liquids, which, amongst other things, also allow high doses of product to be administered by once-daily administration. This is also because the formulation obtained makes any form of delayed or slow-release of the substance contained superfluous.

Lastly, the formulation derived from the "Kefir-type" fermentation process has proved ideal—thereby differing totally from the other calcium and mineral supplements—for constituting a multifunctional "substrate" as a basis for producing dietary supplements in various areas of application for preventive and/or support treatment in various deficiency conditions (poorly nutritional diets, metabolic dysfunctions), immunodeficient states, degenerative diseases (of the bones, dystrophy of the skin), senility, physiological transition periods (menopause).

In all these applications, an important role is probably played by the multifunctional "probiotic" activity of the biological matrix of lactobacilli and yeasts and their immunostimulatory and bioprotective activity as studied by various investigators.

What is claimed is:

1. A process comprising:
   a) preparing a mixture at 18° C. comprising one or more types of pasteurised milk(s) of animal origin;
   b) adding to said mixture 1.5–4.5% by weight of first granules comprising bacteria;
   c) holding the mixture at 18–25° C. for an initial time period ranging from 6 to 12 hours and subsequently adding, after approximately half the process, 1–3% by weight of said pasteurised milk mixture;
   d) adding to the mixture 2.5–6.5% by weight of second granules comprising yeast;
   e) holding the mixture thus obtained at 18–25° C. for a second time period ranging from 6 to 12 hours and adding thereto calcium and/or magnesium and/or potassium in amounts of 0.2–1.2% by weight during the first half of said second time period;
   f) filtering off a residual matrix consisting of the first and second granules and the granules formed during the process itself;
   g) drying the mixture of granules obtained in (f) after said filtration to obtain a powder.

2. The process of claim 1, wherein:
said mixture comprises 50–100% by weight of cow's milk and 0–50% by weight of at least one milk selected from the group consisting of sheep's milk, goat's milk, and mare's milk.

3. The process of claim 1, wherein said first granules comprise per gram:
   Lactobacillus brevis $10^6$–$10^7$
   Lactobacillus casei $10^6$–$10^7$
   Lactobacillus plantarum $10^6$–$10^7$
   Lactobacillus kefir $10^8$–$10^9$
   Lactobacillus kefiranofaciens $10^7$–$10^8$
   Acetobacter aceti $10^6$–$10^7$
   Leuconostoc mesenteroides $10^5$–$10^6$
   Streptococcus lactis $10^4$–$10^5$
   Saccharomyces lactis $10^3$–$10^4$
   Saccharomyces cerevisiae $10^5$–$10^6$
   Saccharomyces fragilis $10^4$–$10^5$ and
   Candida kefir $10^4$–$10^5$.

4. The process of claim 1, wherein said second granules comprise per gram:
   Lactobacillus brevis $10^5$–$10^6$
   Lactobacillus casei $10^5$–$10^6$
   Lactobacillus plantarum $10^5$–$10^6$
   Lactobacillus kefir $10^6$–$10^7$
   Lactobacillus kefiranofaciens $10^6$–$10^7$
   Acetobacter aceti $10^5$–$10^6$
   Leuconostoc mesenteroides $10^4$–$10^5$
   Streptococcus lactis $10^4$–$10^5$
   Saccharomyces lactis $10^5$–$10^6$
   Saccharomyces cerevisiae $10^6$–$10^7$
   Saccharomyces fragilis $10^5$–$10^6$ and
   Candida kefir $10^6$–$10^7$.

5. The process of claim 1, wherein after introduction of said first granules, *Lactobacillus kefir* and *Lactobacillus kefiranofaciens* bacteria are added in amounts of 20–30% by weight of the bacteria of the same species already present in said first granules.

6. The process of claim 1, wherein the initial mixture comprises 80% by weight of cow's milk and 20% by weight of sheep's milk.

7. The process of claim 1, wherein (e) comprises adding calcium to said mixture.

8. The process of claim 1, wherein (e) comprises adding potassium to said mixture.

9. The process of claim 1, wherein (e) comprises adding magnesium to said mixture.

10. The process of claim 1, further comprising
   adding one or more flavouring agent(s).

11. The process of claim 1, further comprising adding a bonding agent to the powder of (g) and compacting said powder into a chewable tablet.

12. A product produced by the process of claim 1.

13. The product of claim 12 in the form of a dry or lyophilized powder.

14. The product of claim 12 in the form of a sachet.

15. The product of claim 12 in the form of a tablet.

16. The product of claim 12 in combination with a liquid.

17. The product of claim 12 in the form of a dietary supplement.

18. A method for the prevention and/or treatment of a disease associated with a calcium, magnesium and/or potassium deficiency comprising administering the product produced by the process of claim 1 to a subject in need thereof.

19. The method of claim 18, wherein said disease is osteoporosis.

20. The method of claim 18, wherein said disease is associated with a calcium deficiency.

21. The method of claim 18, wherein said disease is associated with a magnesium deficiency.

22. The method of claim 18, where said disease is associated with a potassium deficiency.

* * * * *